United States Patent [19]

Matsumura et al.

[11] 4,336,373
[45] Jun. 22, 1982

[54] BIS-PIPERIDINE COMPOUNDS

[75] Inventors: Shingo Matsumura, Kyoto; Hiroshi Enomoto, Nagaokakyo; Yoshiaki Aoyagi, Otsu; Yoshiaki Yoshikuni, Uji; Masahiro Yagi, Kusatsu; Kohei Kura, Omi-Yahata; Ichiro Shirahase, Kyoto all of Japan

[73] Assignee: Nippon Shinyaku Company, Ltd., Japan

[21] Appl. No.: 247,885

[22] Filed: Mar. 26, 1981

Related U.S. Application Data

[63] Continuation-in-part of Ser. No. 229,278, Jan. 28, 1981, abandoned.

[30] Foreign Application Priority Data

Jan. 28, 1980 [JP] Japan .................................. 55-9173

[51] Int. Cl.$^3$ .................. C07D 401/10; C07D 401/12
[52] U.S. Cl. .................................... 542/447; 542/469; 424/267; 546/243

[58] Field of Search ................. 542/469, 447; 546/243

[56] References Cited

U.S. PATENT DOCUMENTS 4,182,767  1/1980  Murai et al. .......................... 546/242
4,220,782  9/1980  Stoltefuss et al. ................... 546/242

OTHER PUBLICATIONS

Matsumura et al. Chem. Abst. 92 (1980) #147138, 110851.

Primary Examiner—Arthur P. Demers
Attorney, Agent, or Firm—Jacobs & Jacobs

[57] ABSTRACT

Bis(2-hydroxymethyl-3,4,5-trihydroxypiperidine-1-yl-propenyl) compounds and their acid addition salts are antihyperglycemic agents. Typical examples are 1,4-bis[3-(2-hydroxymethyl-3,4,5-trihydroxypiperidin-1-yl)prop-2-enyl] benzene and 1,3-bis-{4-[3-(2-hydroxymethyl-3,4,5-trihydroxy-piperidin-1-yl)prop-2-enyl]-phenoxy}propane.

11 Claims, No Drawings

BIS-PIPERIDINE COMPOUNDS

CROSS-REFERENCE

This is a continuation-in-part of Ser. No. 229,278 filed Jan. 28, 1981, now abandoned.

DETAILED DESCRIPTION

This invention relates to the compounds of the formula:

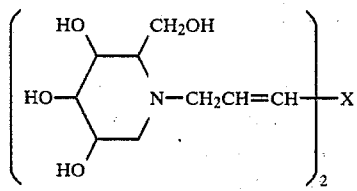

wherein X is a divalent radical selected from the group consisting of phenylene, naphthylene and

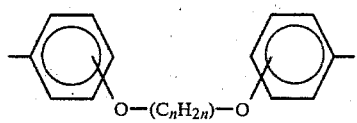

in which n is 2 or 3.

The compounds can also form acid addition salts by reason of the basic piperidine nitrogen atom. Physiologically acceptable nontoxic acid addition salts of this type include those derived for organic and inorganic acids such as hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The two bis group can be directly bound to a phenyl ring ortho, meta, or para to one another. Similarly, the two bis groups may be on the same or different ring of naphthalene. When the bis groups are bound to the $C_6H_4O(CnH_{2n})OC_6H_4$ bridge, the orientation of the individual bis groups on each phenylene ring to the $-O(CnH_{2n})O-$ bridge can also be ortho, meta or para.

The compounds of this invention and their salts are antihyperglycemic agents and medicinally useful. The property manifests itself through inhibition of an increase of blood sugar level increase, the compounds are very useful as prophylatic and therapeutic agents for hyperglycemic conditions encountered in, for example, diabetes, arteriosclerosis, obesity, gastritis, peptic ulcer, duodenum ulcer, and the like. The toxicity of the compounds is extremely favorable.

The compounds of the present invention are generally administered orally in any of the usual pharmaceutical forms. These include solid and liquid oral unit dosage forms such as tablets, capsules, powders, suspensions, solutions, syrups and the like, including sustained release preparations. The term unit dosage form as used in this specification and the claims refer to physically discrete units to be administered in single or multiple dosage to animals, each unit containing a predetermined quantity of the piperidine derivative in association with the required diluent, carrier or vehicle. The quantity of the piperidine derivative is that calculated to produce the desired antihyperglycemic effect upon administration of one or more of such units.

Powders are prepared by comminuting the compound to a suitable fine size and mixing with a similarly comminuted diluent pharmaceutical carrier. Although this can be an edible carbohydrate material as for example starch, generally such are avoided in view of the pharmaceutical use. Flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the piperidine compound, suitably comminuted, with a diluent or base such as kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, polymeric mineral and a polish coating of wax can be provided. Dyestuffs can be added to these coatings to distinguish different unit dosages.

Oral fluids such as elixirs can be prepared in unit dosage form so that a given quantity, e.g., a teaspoonful, contains a predetermined amount of the compound. Suspensions can be formulated by dispersing the compound in a nontoxic vehicle in which it is soluble.

The compounds can also be administered in foodstuffs to minimize increases in blood sugar.

The compounds can also be given to livestock, by admixture with their feed, in their drinking water or by conventional veterinary formulations.

The compounds are administered in the conventional manner to humans and other animals, in each case carefully titrating the dose to the age, condition and response of the recipient.

The antihyperglycemic activity can be conveniently observed in well-known and widely employed laboratory models, as for example the depression of blood sugar levels in glucose loaded rats. The compounds all show a percent inhibition of more than 80% when they are orally administered to rats in a dose of 1 mg/kg together with 2 g/kg of sucrose and the percent inhibition of blood sugar level increase is measured 30 minutes later. The following data are representative:

| No. | Compound | % Inhibition |
| --- | --- | --- |
| 1 | p-phenylene | 89 |
| 2 | m-phenylene | 87 |
| 3 | 2,6-naphthylene, | 84 |
| 4 | 1,5-naphthylene | 80 |
| 5 | 1,3-bis(1,4-phenyleneoxy)propane | 87 |
| 6 | 1,2-bis(1,3-phenyleneoxy)ethane | 85 |

In synthesizing these compounds, 2-hydroxymethyl-3,4,5-trihydroxypiperidine, which is known as moranoline, with or without protection of the hydroxy groups by a suitable group such as an acetyl, benzoyl, benzyl, tetrahydropyranyl, methoxymethyl or methoxyethoxymethyl group as a starting material, is allowed to react with an activated derivative of a bis-allyl alcohol of benzene, naphthalene or diphenoxyalkane, as for example a bis-(3-halo-1-propenyl)benzene, bis-(3-halo-1-propenyl)naphthalene or bis[(3-halo-1-propenyl)-phenoxy]alkane, with an acid binding agent such as potassium carbonate or sodium hydrogen carbonate. Lower alcohols, lower polyhydric alcohols, polar aprotic solvents such as DMF and DMSO, and the like are advantageously used as a solvent.

The compounds may also be synthesized by the reductive alkylation, i.e., reduction of a substituted aldehyde and moranoline, or by reduction of these using a boron hydride complex. They can also be produced by preparing an amide from moranoline having protected hydroxyl groups and an appropriate acid, and reducing the amide.

The following examples will serve to further typify the nature of the invention. These examples should not be construed however as a limitation on the scope of the invention.

EXAMPLE I 1,4-Bis-[3-(2-hydroxymethyl-3,4,5-trihydroxypiperidin-1-yl)prop-2-enyl]benzene Vinyl magnesium bromide prepared from 60 g of vinyl bromide and 14 g of metallic magnesium is dissolved in about 200 ml of tetrahydrofuran (to be abbreviated as THF herein below). With stirring, a solution of 25 g of terephthalaldehyde in 200 ml of THF is added dropwise to the above solution over 30 minutes. After the addition, the reaction mixture is refluxed for 30 minutes with stirring. After cooling, a small amount of water is added for decomposition while cooling the solution with ice. Ethyl acetate is added to the reaction product, and the insoluble materials are removed by filtration. The ethyl acetate layer is washed with water and then concentrated to obtain 21 g of the reaction product as a light yellow oil. The resulting product is dissolved in 250 ml of ethyl acetate, and with stirring, 30 g of thionyl chloride is added with stirring. After the addition, the mixture is heated under reflux for 2 hours. After cooling, the reaction product is evaporated to dryness under reduced pressure, and the remaining crystalline substance is recrystallized from a small amount of ethyl acetate. The amount yielded 15.8 g. Melting point 124°–219° C.

Moranoline (20 g) and 10 g of sodium hydrogen carbonate are dissolved and suspended in 200 ml of DMSO, and with stirring, 6.5 g of benzene-1, 4-bisallyl chloride obtained above is added. The mixture is stirred at 22° to 25° C. for 4 hours. The involuble materials are then removed by filtration. The filtrate is diluted with 1000 ml of water, and then washed with chloroform. The product is passed through a column of an ion-exchange resin [Dowex 50 W×4 (H), 400 ml]. The column is washed with water, and eluted with 0.2% aqueous ammonia to recover the unreacted moranoline. Then, the desired final product is eluted with methanol containing 50% of water and 2% of ammonia. The eluate is dried to a solid under reduced pressure, and the remaining crystals are recrystallized from 50% methanol. Melting point 256°–259° C. (decomp.), $[\alpha]_D^{24} = -61.1°$ (DMSO), amount yielded 7.1 g, hydrochloride: recrystallized from methanol. Melting point 222°–225° C., $[\alpha]_D^{24} = -25.9°$ (water).

EXAMPLE 2

1,3-Bis-[3-(2-hydroxymethyl-3,4,5-trihydroxypiperidin-1-yl)prop-2-enyl]benzene

By substituting isophthaldehyde for terephthalaldehyde in the procedure of Example 1, the title compound is obtained, m.p. 189°–192° C. (dec.), $[\alpha]_D^{24} = -42.3°$ (DMSO).

EXAMPLE 3

2,6-Bis-[3-(2-hydroxymethyl-3,4,5-trihydroxypiperidin-1-yl)prop-2-enyl]naphthalene Ten grams of naphthalene-2, 6-dialdehyde is reacted with about 18 g of vinyl magnesium bromide in the same way as in Example 1 to obtain 10.6 g of the reaction product as a yellowish brown oil. The resulting reaction product is reacted with 15 g of thionyl chloride in 150 ml of chloroform. The resulting reaction product is recrystallized from ethyl acetate to obtain naphthalene-2, 6-bisallyl chloride. Melting point 151°–158° C. The amount yielded 8.1 g.

Moranoline (20 g) is dissolved in 200 ml of DMSO, and 10 g of sodium hydrogen carbonate and 8.0 g of the reaction product obtained above are added. They are reacted in the same way as above. After the reaction, the reaction mixture is diluted with 800 ml of water and washed with chloroform. Then, ammonium sulfate is added to salt out the product. On standing at room temperature, crystals precipitate. The crystals are recrystallized from methanol. Melting point 268°–273° C. (decomp.). $[\alpha]_D^{24} = -47.8°$ (DMSO), amount yielded 8.1 g.

EXAMPLE 4

1,5-Bis-[3-(2-hydroxymethyl-3,4,5-trihydroxypiperidin-1-yl)prop-2-enyl]naphthalene The title compound, m.p. 253°–260° C., $[\alpha]_D^{24} = -45.4°$ (DMSO), is obtained from naphthalene-1,5-dialdehyde according to the procedure of Example 3.

EXAMPLE 5

1,3-Bis-{-[3-(2-hydroxymethyl-3,4,5-trihydroxypiperidin-1-yl)prop-2-enyl]phenoxy}propane p-Hydroxybenzaldehyde (18 g), 10 g of 1,3-dibromopropane, and 21 g of anhydrous potassium carbonate are heated at 80° C. for 4.5 hours with stirring in 100 ml of DMF. The reaction mixture is diluted with 900 ml of water, and extracted with ether. The extract is concentrated to dryness, and the remaining crystals are recrystallized from benzene. The amount yielded 18 g. The resulting crystals are dissolved in 50 ml of THF, and the solution is added dropwise to a solution of about 30 g of vinyl magnesium bromide in 200 ml of THF. After the addition, the mixture is heated at 40° to 50° C. for 30 minutes with stirring. After cooling with ice, a small amount of water is added for decomposition. The insoluble materials are removed by filtration, and the filtrate is dried to a solid under recuded pressure. The residue is extracted with ether. The extract is recrystallized from benzene. The amount yielded 17 g.

The resulting reaction product (6.0 g) is dissolved in 100 ml of ether, and 4.2 g of thionyl chloride is added dropwise with stirring while cooling the solution with ice. Immediately then, the reaction product is evaporated to dryness under reduced pressure at less than 20° C. To the resulting reaction product is added 50 ml of DMSO having dissolved therein 6 g of moranoline, and 5.0 g of sodium hydrogen carbonate is added. The mixture is stirred overnight at room temperature. Then, the product is diluted with 500 ml of water, acidified with acetic acid, washed with chloroform, and passed through a column of an ion-exchange rasin [Amberlite IR-120 (H) about 150 ml]. The column is washed with water, and then eluted with 0.5% aqueous ammonia. The eluate is evaporated to dryness under reduced pressure, and the remaining crystalline substance is extracted with hot ethanol. Hot ethanol-soluble materials are collected, and chromatographed on a silica gel column using a 3:1 mixture of chloroform and methanol as an eluent. The purified product is recrystallized from ethanol. Melting point 202°–205° C. $[\alpha]_D^{24} = -33.6°$ (DMSO), the amount yielded 1.9 g.

EXAMPLE 6

1,2-Bis-{3-[3-(2-hydroxymethyl-3,4,5-trihydroxypiperidin-1-yl)prop-2-enyl]phenoxy}ethane The title compound, demonstrating a m.p. of 210°–213° C. after recrystallization from ethanol and an $[\alpha]_D^{24} = -29.8°$ (DMSO), is obtained from m-hydroxybenzaldehyde and 1,2-dibromoethane according to the procedure of Example 5.

What is claimed is:

1. A compound of the formula:

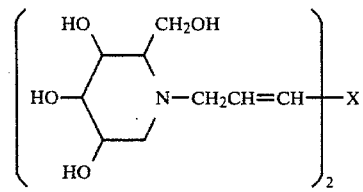

wherein X is a divalent radical selected from the group consisting of phenylene, naphthylene and

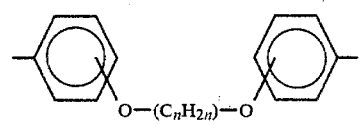

in which n is 2 or 3.

2. A compound according to claim 1 wherein X is phenylene.

3. The compound according to claim 2 wherein X is p-phenylene.

4. The compound according to claim 2 wherein X is m-phenylene.

5. A compound according to claim 1 wherein X is naphthylene.

6. The compound according to claim 5 wherein X is 2,6-naphthylene.

7. The compound according to claim 5 wherein X is 1,5-naphthylene.

8. A compound according to claim 1 in which X is

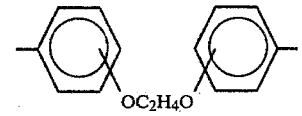

9. The compound according to claim 8 which is 1,2-bis-{3-[3-(2-hydroxymethyl-3,4,5-trihydroxypiperidin-1-yl)prop-2-enyl]phenoxy}-ethane.

10. A compound according to claim 1 in which X is

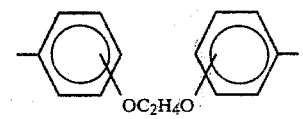

11. The compound according to claim 10 which is 1,3-bis-{4-[3-(2-hydroxymethyl-3,4,5-trihydroxypiperidin-1-yl)prop-2-enyl]phenoxy}-propane.

* * * * *